United States Patent [19]

Gil et al.

[11] Patent Number: 5,106,737
[45] Date of Patent: Apr. 21, 1992

[54] PROCESS FOR OBTAINING IRONE BY MICROBIOLOGICAL ROUTE

[75] Inventors: Gérard Gil, Aubagne; Jean Le Petit, Allauch, both of France

[73] Assignee: Societe Nationale Elf Aquitaine, Paris, France

[21] Appl. No.: 658,673

[22] Filed: Feb. 21, 1991

[30] Foreign Application Priority Data

Feb. 22, 1990 [FR] France ................... 90 02213

[51] Int. Cl.$^5$ .................. C12R 1/645; C12P 7/26
[52] U.S. Cl. ................... 435/148; 435/259; 435/911
[58] Field of Search .......... 435/148, 911, 259

[56] References Cited

U.S. PATENT DOCUMENTS

| | | | |
|---|---|---|---|
| 4,390,557 | 6/1983 | Krasnobajew | 435/148 |
| 4,963,480 | 10/1990 | Belcour et al. | 435/148 |
| 4,981,796 | 1/1991 | Ogura et al. | 435/156 |

FOREIGN PATENT DOCUMENTS 2620702  3/1989  France .

OTHER PUBLICATIONS

ATTC Catalogue Fungi/Yeasts 16th ed. 1984, p. 52, Lib of Cong No. 84-71496, ATTC 12301 Parklawn Drive, Rockville, Md. 20852.

Bagdasarova et al.: "*Bioconversion of terpenoids by iris sibirica cell cultures*", Chemical Abstracts, vol. 110, 1989, p. 504, No. 73846e.

"*List of Cultures 1987*", Institute of the Royal Netherlands Academy of Arts and Sciences, pp. 55-56.

*Primary Examiner*—Herbert J. Lilling
*Attorney, Agent, or Firm*—Foley & Lardner

[57] ABSTRACT

The object of the present invention is a process for obtaining irone by microbiological route.

The precursors extracted from fresh iris rhizomes are subjected to the action of a fungus of the genus Botryotinia.

19 Claims, No Drawings

PROCESS FOR OBTAINING IRONE BY MICROBIOLOGICAL ROUTE

The present invention relates to a process for the preparation of irone, the mixtures of the three isomers of which, α, β, γ, are used in the food industry and in the cosmetics and perfume industries for their odour of violets.

At the time they are harvested, the iris rhizomes hardly contain any irone, and it is during prolonged storage that the formation of the latter occurs, probably by oxidative conversion of triterpenes initially present.

In the usual process for obtaining irone, it is thus necessary to wait more than two years after harvesting the rhizomes in order to be able to extract a reasonable amount of irone by steam stripping or by using an organic solvent.

Recently, a process has been suggested in the patent application FR-A-2 620 702 which makes prolonged storage unnecessary, a process characterized in that the precursors of irone are extracted from the rhizomes shortly after harvesting by means of a lipophilic solvent, and are then subjected to a chemical oxidation which results in the molecules of irone.

This process possesses the disadvantage of making use of chemical reagents which preclude the use of the irone thus obtained in the food industry and it was desirable to find a natural process of degradation such as a microbiological process. Nevertheless, finding microorganisms capable of effecting this conversion, as do the plant enzymes during storage, was not obvious.

Aerobic micro-organisms have now been found which degrade the precursors within a few days, without at the same time degrading extensively the irone formed, and which give yields of irone based on the quantity of iris rhizomes used which are markedly higher than those obtained with the conventional process. This is all the more valuable since the quantity of iris rhizomes available on the European market is actually falling without a diminution in the demand for irone.

The process according to the invention consists of converting the precursors of irone present in fresh iris rhizomes by subjecting them to the action of a micro-organism of the genus Botryotinia, also named Sclerotinia, the imperfect form of which is designated Botrytis. These fungi are described in the monograph by M. B. Ellis—Hyphomycetes p. 178-184 (1971)—Commonwealth Mycological Institute.

A common species of this filamentous fungus, various strains of which may be obtained from the international collections of micro-organisms, is *Botryotinia convulata*, but other species, such as *B. draytonii*, *B. ficariarum* or *B. fuckeliana* may be suitable; these latter are described in: Microfungi on land plants. An Identification Handbook—M. B. Ellis and J. P. Ellis—1985—Croom Helm—London.

It is possible to use the entire micro-organism in its culture medium or simply the mycelium; it is also possible to use the medium in which the fungus was cultured, after removal of the mycelium.

The culture medium may be one of those usually used for this type of fungi, i.e. water containing a carbon source, a nitrogen source and metal salts. As carbon source, mention may be made of sugars such as glucose, maltose or lactose of also glycerol; as nitrogen source, mention may be made of cassein, amino acids or peptides and proteins including gelatin and hydrolysed gelatin, a malt extract or a maize cob, a meat extract, urea, or soya bean four; as metal salts, mention may be made of phosphates, citrates or acetates of sodium, magnesium, copper, manganese or iron and, better still, a mixture of iron, copper and manganese salts. The pH of the culture medium is acidic or neutral, from 3.5 to 7 and, preferably, from 5.5 to 6; optionally, the pH of the medium may be maintained constant with a phosphate, phthalate or Tris buffer or it may be adjusted as necessary during the culture of the fungus. The temperature of the medium during culture is that which is the most favourable for the micro-organism; it is usually between 15° C. and 30° C., and the conversion reaction of the irone precursors will preferably as performed at this temperature.

The preliminary step of extraction of the precursors from fresh rhizomes, possibly dried in particular in order to facilitate their transport, is carried out by suspending the crushed or ground rhizomes in an organic solvent usually used in the flavouring industry such as the alcoholic solvents methanol or ethanol, the chlorinated solvents, methylene chloride or dichloroethane, the aromatic or aliphatic hydrocarbons hexane or benzene; it is also possible to use mixtures of solvents or carry out two successive extractions with different solvents, for example with a solvent miscible with water and another immiscible with water. It is preferable to use alcoholic or chlorinated solvents and, in particular, methanol and methylene chloride. It is possible to remove the water-soluble substance drawn off during a first extraction by redissolving the extract in a solvent immiscible with water and by washing this organic phase with water before removing the solvent in order to obtain the extract which will be subjected to the action of the fungus.

*Iris germanica, pallide* or *florentina* of various origins such as Morocco or Italy may be used. It is known that the yield of irone and the proportion of the isomers in the product obtained may vary appreciably with the species, the origin and the maturity of the irises used; in all cases, the process according to the invention gives markedly more favourable results than the conventional process.

According to the invention, the extract, preferably suspended in water or dissolved in a small volume of hydrophilic organic solvent such as acetone, an alcohol or dioxane, is introduced into the medium in which the fungus has been cultured until the maximal biomass is obtained, i.e. about 48 hours, at the ratio of 1 g to 20 g of extract per liter of medium; as is usual in this field, in view of the insolubility of the extract in the medium, it is possible to introduce simultaneously a small amount of a surfactant such as a fatty acid ester of sorbitol, for example a Tween, as well as an anti-foaming agent such as a silicone oil, a polyalkyleneglycol, soya or maize oil. The medium is stirred and serated, if necessary for example 20 to 60 h at 20° C.; the cells are then removed by filtration and the irone obtained is separated by steam stripping or it is extracted with an organic solvent immiscible with water. The optimal reaction time and temperature depend on the operating conditions: material, nature and concentration of the reagents, species and strain of fungi and the specialist will be able to determine by means of preliminary tests the optimal parameters of the reaction, knowing that the irone formed may be degraded by the fungus; the course of the reaction may be monitored, in particular, by gas chromatography.

The biomass necessary to convert a given quantity of extract will be less if, in accordance with a known induction technique, the extract is introduced into the preculture and culture medium of the fungus at a low concentration of 0.05 to 0.1%.

Moreover, the yields of irone are markedly improved, if, at the end of culture, a non-ionic surfactant such as the polyol esters of fatty acid as Tween, or the polyalkyleneglycols such as octylphenoxypolyethoxyethanol or Triton X, are introduced in order to obtain permeable cell membranes, before introducing the extract to be degraded. These agents are usually used at a concentration of 0.05% to 0.25%.

According to another feature of the invention, the biomass may be separated from the culture medium by filtration before introducing the extract into it, eventually after having made the membranes permeable.

Although the conversion yields are less good, it is also possible to separate the mycelium from the culture medium, optionally after having made the membranes permeable, and to suspend it is a buffered aqueous solution, preferably containing 5 to 15 g/l of glucose, and to introduce into this medium the extract to be converted, preferably in the presence of a surfactant.

According to another feature of the invention, the process is implemented with immobilized micro-organisms, which enable it to operate continuously; the immobilization is performed in a known manner either by cultivating the fungus in a medium containing a solid such as beads, disks, rings or any other form of glass or inert polymer to which the growing mycelium can attach itself, or by separating the fungus or the mycelium from its culture medium and by incorporating it in porous matrices, formed by chemical cross-linking of suitable monomers or by coacervation of polymers.

In what follows, examples of the implementation of the invention are described.

First, the extraction of the precursors is illustrated:

2.5 kg of rhizomes of iris Pallida of Italy, dried but still containing 6% water, are cleaned and placed in a 60 l stainless steel vessel equipped with a rotating paddle stirrer and containing 24 l of 96% ethanol; the mixture is maintained at the reflux temperature of the solvent for 20 h, then cooled to room temperature and filtered; the filtrate is concentrated to dryness in a vacuum; the solids filtered off are reintroduced in 12 l of methylene chloride in the vessel and the mixture is maintained at the reflux temperature of the solvent for 20 h, then filtered at room temperature, the filtrate is concentrated to dryness in a vacuum and the residue, combined with the previous one, is redissolved in 2 l of methylene chloride. The organic phase is washed twice with water and evaporated to dryness to give 1 kg of dry extract.

Subsequently, the action of the micro-organism is illustrated. Strains of *Botryotinia convulata*, available from the collection of the Centraalbureau Voor Schimmelcultures Baarn (CBS), Delft (Holland), under the references 285-38, 286-38, 428-38, were used.

EXAMPLE 1

Culture of the micro-organism

The fungus stored in PDA (Potato Dextrose Agar) medium, marketed by Merieux (France) is used to inoculate 100 ml of a preculture medium at pH 5.7, constituted of 15 g of malt extract per liter of water, 10 g/l of glucose, 2 mg/l of copper sulfate, 2 mg/l of ferric and ammonium citrates and 2 mg/l of zinc chloride with a drop of an acetone solution of the extract; after being stirred for 48 h at 20° C., the preculture is introduced into 800 ml of culture medium at pH 5.7, constituted of 25 g/l of corn steep liquor and 2 mg/l of copper sulfate, ammonium and ferric citrates and zinc chloride, with 1 ml of an acetone solution of the extract. After being stirred for 48 h at 20° C., 0.1% Triton X 100 is introduced into the medium followed, 2 h later, by 5 g of extract in emulsion in 10 ml of water and 1 ml of acetone containing 0.2% Tween 80. The medium is incubated at 20° C., then the irone is separated by steam distillation. The quantity of irone obtained after assays lasting from 12 to 72 h, measured by gas chromatography, is shown in table 1; it is expressed in grams of irone per kilo of dry material of the rhizomes used to prepare the treated extract.

TABLE 1

| Duration | g of irone/kg of dry rhizome extract |
|---|---|
| 12 h | 1.15 |
| 24 h | 1.2 |
| 36 h | 2.2 |
| 48 h | 2.3 |
| 72 h | 1.1 |

EXAMPLE 2

The experiment is repeated using the same procedure as that of example 1 except the Triton is not introduced at the end of culture. In this case, only 1.1 g of irone are obtained after 48 h.

We claim:

1. A microbiological process for obtaining irone, which comprises the steps of:
   (a) incubating a lipophilic extract of fresh iris rhizomes, obtained with a solvent selected from the group consisting of alcoholic solvents, chlorinated solvents, aliphatic hydrocarbons, aromatic hydrocarbons, and mixtures thereof, in an aqueous culture medium, with a culture of a fungus of the genus Botryotinia; whereby irone precursors in said extract are oxidized to irone; and
   (b) recovering resultant irone.
2. A process according to claim 1, wherein said solvents are selected from the group consisting of dichloroethane, hexane, benzene, and mixtures thereof.
3. A process according to claim 1, wherein said solvent is selected from the group consisting of methanol, ethanol and methylene chloride.
4. A process according to claim 1 wherein the pH of said culture medium lies between 5.5 and 6.
5. A process according to claim 1, wherein said culture medium of the fungus comprises an iron salt.
6. A process according to claim 1, wherein a preculture medium is first inoculated with said fungus, and subsequently said culture medium is inoculated with said fungus contained in said preculture medium.
7. A process according to claim 1, wherein the fungus is treated with an agent to give permeable cell membranes before its action on the said lipophilic extract.
8. A process according to claim 1, wherein the fungus is treated with Triton X before its action on the said lipophilic extract.
9. A process according to claim 1, wherein the fungus belongs to said species *Botryotinia convulata*.
10. A process according to claim 9, wherein said culture medium of the fungus comprises an iron salt.

11. A process according to claim 9, wherein a preculture medium is first inoculated with said fungus, and subsequently said culture medium is inoculated with said fungus contained in said preculture medium.

12. A process according to claim 9, wherein the fungus is treated with an agent to give permeable cell membranes before the action of said fungus on said lipophilic extract.

13. A process according to claim 9, wherein the growth of said fungus is induced by addition of a small amount of said rhizome extract to the culture medium containing an iron salt and the cell membranes are treated with an agent to give permeable cell membranes before its action on said lipophilic extracts.

14. A process according to claim 6, wherein the growth of said fungus is induced by the addition of a small amount of said rhizome extract to the preculture and culture medium of the fungus.

15. A process according to claim 11, wherein the fungus growth is induced by addition of a small amount of said rhizome extract into the preculture and culture medium of the fungus.

16. A process according to claim 1, wherein a surfactant, anti-foaming agent, or mixtures thereof are introduced into the medium during step (a).

17. A process according to claim 1, wherein said lipophilic extract of fresh iris rhizomes is introduced into the medium suspended in water or dissolved in a hydrophilic organic solvent.

18. A process according to claim 10, wherein said iron salt is introduced into said culture medium at a pH of 5.5 to 6.

19. A process according to claim 10, wherein said incubation is accomplished at a temperature of 15° C. to 30° C.

* * * * *